US006294328B1

(12) United States Patent
Fleischmann et al.

(10) Patent No.: US 6,294,328 B1
(45) Date of Patent: Sep. 25, 2001

(54) **DNA SEQUENCES FOR STRAIN ANALYSIS IN *MYCOBACTERIUM TUBERCULOSIS***

(75) Inventors: Robert David Fleischmann, Gaithersburg; Owen Richardson White, Rockville; Claire Marie Fraser; John Craig Venter, both of Potomac, all of MD (US)

(73) Assignee: The Institute for Genomic Research, Rockville, MD (US)

( * ) Notice: Subject to any disclaimer, the term of this patent is extended or adjusted under 35 U.S.C. 154(b) by 0 days.

(21) Appl. No.: 09/103,840

(22) Filed: Jun. 24, 1998

(51) Int. Cl.$^7$ .............................. C12Q 1/68; C07H 21/04; C07H 21/02

(52) U.S. Cl. ............................ 435/6; 536/22.1; 536/23.1; 536/24.1

(58) Field of Search ..................... 435/6, 91.2; 536/22.1, 536/23.1, 24.3

(56) References Cited

PUBLICATIONS

Philipp et al. "Physical Mapping of Mycobacterium bovis BCG Pasteur reveals differences from the genome map of Mycobacterium tuberculosis H37Rv and from M. bovis", Microbiology, vol. 142, pp. 3135–3145, 1996.*

Pevear et al, "Insights into Theiler's Virus Neurovirulence Based on a Genomic Comparison of the Neurovirulent GDVII and less virulent BeAn Strains", Virology, pp. 1–12, 1988.*

NIAID Mycobacterial Genome Workshop Exploiting the TB Genome Executive Summary, Bethesda, MD, pp. 1–2, Sep. 15, 1997.*

Delcher et al., "Alignment of whole genomes", Nucleic Acids Research, vol. 27(11), pp. 2639–2376, 1999.*

Behr et al., "Comparative Genomics of BCG Vaccines by Whole–Genome DNA Microarray", Science, 284:15201523 (1999).

Cole et al., "Deciphering the Biology of Mycobacterium Tuberculosis from the Complete Genome Sequence", Nature, 393:537–544 (1998).

Fleischmann et al "Whole–Genome Random Sequencing and Assembly of Haemophilus Influenzae Rd", Science, 269:496–512 (1995).

Gordon et al., "Identification of Variable Regions in the Genomes of Tubercle Bacilli Using Bacterial Artificial Chromosome Arrays", Molecular Microbiology, 32(3):643–655 (1999).

Mahairas et al., "Molecular Analysis of Genetic Differences Between Mycobacterium Bovis BCG and Virulent M. Bovis", J. Bacteriology, 178(5):1274–1282 (1996).

Phillip et al. "Physical Mapping of Mycobacterium Bovis BCG Pasteur Reveals Differences from the Genome Map of Mycobacterium Tuberculosis H37Rv and from M. Bovis", Microbiology, 142:3135–3145 (1997).

Sreevatsan et al., "Restricted Structural Gene Polymorphism in the Mycobacterium Tuberculosis Complex Indicates Evolutionarily Recent Global Dissemination", Proc. Natl. Acad. Sci., USA, 94:9868–9874 (1997).

Valway et al., "An Outbreak Involving Extensive Transmission of a Virulent Strain of Mycobacterium Tuberculosis", The New J. of Medicine, 338(10):633–639 (1998).

Wilson et al., "Exploring Drug–Induced Alterations in Gene Expression in Mycobacterium Tuberculosis by Microarray Hybridization", Proc. Natl. Acad. Sci., 96(22):12833–12838 (1999).

S. Sreevatsan et al., "Restricted Structural Gene Polymorphism in the Mycobacterium Tuberculosis . . . " Proc. Natl. Acad. Sci, USA, 94, pp. 9869–9874 (1997).

S. Cole et al., "Deciphering the Biology of Mycobacterium Tuberculosis from the Complete Genome Sequence", Nature, 393, pp. 537–544 (1998).

S. Valway et al., "An Outbreak Involving Extensive Transmission of a Virulent Strain of Mycobacterium Tuberculosis", New England Journal of Medicine, 338, pp. 633–639 (1988).

W. Philipp et al., "An Integrated Map of the Genome of the Tubercle Bacillus Mycobacterium Tuberculosis . . ." Proc. Natl. Acad. Sci. USA, 93, pp. 3132–3137 (1996).

* cited by examiner

*Primary Examiner*—Jeffrey Fredman
*Assistant Examiner*—Arun Kr. Chakrabarti
(74) *Attorney, Agent, or Firm*—Morrison & Foerster LLP

(57) ABSTRACT

The present invention is directed to novel methodology whereby different populations of the tuberculosis bacterial pathogen, *Mycobacterium tuberculosis,* or related Mycobacteria, can be genetically classified in relation to other isolates. Sites in the genome of Mycobacterium, which define previously unrecognized points of variability, are disclosed. The existence of this variability is of use to the clinician in order to consistently determine the identity of isolates of Mycobacterium responsible for individual cases of disease or disease outbreaks, thus suggesting appropriate choices for treatment protocols.

11 Claims, No Drawings

US 6,294,328 B1

DNA SEQUENCES FOR STRAIN ANALYSIS IN *MYCOBACTERIUM TUBERCULOSIS*

FIELD OF THE INVENTION

The present invention is directed to novel methodology, and DNA sequence libraries that result therefrom, whereby different strains of the tuberculosis bacterial pathogen, *Mycobacterium tuberculosis*, can be definitively identified, based upon the identification of differences in their respective DNA sequences. The invention has valuable application in the fields of tuberculosis genetics, epidemiology, patient treatment, and epidemic monitoring.

Reported Developments

Although certain chemotherapy and vaccine protocols have become available for he treatment of tuberculosis, the disease continues to claim more lives per year than any other infectious disease (see S. Cole et al., *Nature*, 393, pp.537–544, 1998). In fact, despite the widespread availablity of health measures in the industrialized world, the incidence of tuberculosis has been spreading in both the industrialized and developing nations. This increased incidence is of particular concern in view of the emergence of novel drug-resistant strains, and the strong presence of the disease in HIV-afflicted patients.

It has been the recognized understanding in the art (see S. Cole et al., and S. Sreevatsan et al., *Proc. Natl. Acad. Sci, USA*, 94, pp.9869–9874, 1997) that *M. tuberculosis* is a member of a complex of closely related species. The complex is understood to substantially lack interstrain genetic diversity, nucleotide changes being very rare. It has thus been the perception that both vaccine development and strain characterization would continue to be difficult, given that most proteins were expected to be identical between strains.

These difficulties are further compounded by the growth characteristics of *Mycobacterium tuberculosis* in patients and in culture. Cell growth is characterized by several unusual features including, for example, (1) very slow growth (a doubling time of circa 24 hours which is much slower that other bacteria such as *E. coli*, that have a doubling time of perhaps 30 minutes), (2) the capacity to become dormant in infected tissue for long periods of time, (3) the capacity to remain present at low density levels that probably avoids immune detection; and (4) the presence of unusual and complex cell wall components that probably contribute to pathogenicity and inflammation.

The present invention is directed to the discovery that, notwithstanding the above observations, very substantial differences in the DNA sequences between related Mycobacterium strains can be identified. Additionally, according to the practice of the present invention, it is not required that such DNA sequence differences be localized to protein encoding sequences.

SUMMARY OF THE INVENTION

According to the practice of the present invention, there is provided a nucleotide by nucleotide comparison between a well-recognized, but long ago characterized virulent strain, and a recent isolate correlated with a severe and persistent outbreak in the United States. Sequence differences bewtween the two strains are substantial, and point to loci in the DNA of Mycobacterium that can be used as markers for strain variation and characterization. Given that different strains have different susceptibilities to various therapeutic programs, providing proper identification of a strain responsible for a particular infection is of great importance to physicians.

Accordingly, there is provided a method of evaluating the virulence of a first strain of *Mycobacterium tuberculosis*, comprising the step of determining the nucleotide sequence of said strain at positions in the genome thereof, that correspond to positions where *M. tuberculosis* strains CDC 1551 and H37Rv differ as to sequence, and determining whether the nucleotide sequence of said first strain shows greater homology, at said positions, to the sequence of strain CDC 1551 or H37Rv.

BRIEF DESCRIPTION OF THE FIGURES AND SEQUENCES

FIG. 1 provides a comparison of the complete DNA sequence of the H37Rv strain of *M. tuberculosis* with that of the CDC 1551 strain thereof. The entire DNA sequence of H37Rv is provided as SEQ ID NO:1, and represents the website-published version thereof as updated and available in January 1998.

FIG. 2 provides the DNA sequence of *M. tuberculosis* strain CDC 1551.

DETAILED DESCRIPTION OF THE INVENTION

According to the practice of the invention, it has been surprisingly determined that there are substantial nucleotide sequence differences between the genome of *M. tuberculosis* strains CDC 1551 and H37Rv. These differences extend to protein-encoding DNA and non-coding DNAs such as those for rRNA, tRNA, and what may be structural elements within the chromosome such as certain repeat sequences.

According to the practice of the invention, the similarity of a strain to H37Rv, a reference standard, may be assessed by evaluating nucleotide sequence homology at the same sites where CDC 1551 and H37Rv differ (FIG. 1, see below). Such homology may be evaluated by a direct comparison of nucleotide sequences or may be approximated by a comparison of restriction patterns, such as derived through restriction fragment length polymorphism analysis. There is thus provided a way to determine the similarity of an unknown or recently evolved strain of Mycobacterium, and most typically of species tuberculosis, to previously evolved strains in order to assess the likelihood that previously utilitzed therapies such as pharmaceuticals or antibody-derived products will or will not be effective. Reference may also be made to therapies effective against the CDC 1551 strain in the event significant similarities to that strain are found.

EXAMPLE 1

Comparison of Sequences

The well known H37Rv strain of *M. tuberculosis* is described in W. Philipp et al., *Proc. Natl. Acad. Sci, USA*, 93, pp.3132–3137, 1996 and also S. Cole, et al., *Nature*, 393, pp.537–544, 1998. The entire DNA sequence thereof as depicted by SEQ ID NO:1 herein represents the sequence available in January 1998 at the website of the Sanger Centre, Wellcome Trust Genome Campus, Hinxton, UK.

Strain CDC 1551 (see FIG. 2 herein for the DNA sequence) is described in S. Valway et al., New England Journal of Medicine, 338, pp.633–639m 1998 and is the highly virulent strain responsible for a serious highly contagious outbreak in Kentucky and Tennessee, USA during the mid-1990's. FIG. 2 discloses the encoding DNA sequence thereof as a series of consecutive subsequences, and also provides (see the cover sheet for FIG. 2, "Explanation of Data") the alignment of the CDC 1551 sequence with the H37Rv sequence. Although numbered quite differently, the "start" and "end" positions show the correspondence between the two sequences.

Reference may then be made to FIG. 1, which using the numbering systems for the two encoding polynucleotides, provides a comparison of the CDC 1551 and H37Rv nucleotide sequences with respect to the additions, deletions, changes, and the like, that cause the sequences to differ. In FIG. 1, the H37Rv position is indicated on the left, and the base change(s) therein needed to generate therefrom the CDC 1551 sequence is indicated, as is the nucleotide position in the CDC 1551 sequence where the change appears.

Thus, in a few examples of the sequence comparison provided by FIG. 1:

(a) for the first item on page 1: nucleotide "C" is deleted at H37Rv position 1118, and the deletion appears one nucleotide downstream from position 152171 in CD 1551, to bring the sequences into alignment;

(b) for the second item, by changing H37Rv position 3229 to a "C", the CD 1551 sequence results with a "C" appearing at its position 154282; and (c) on page 5, near the bottom, by deleting nucleotides "T,A" at positions 182425 and 182426 of the H37Rv sequence, the CD 1551 sequence results starting immediately after position 333536.

As aforementioned, additional explanatory material is found in the Appendix A.

SEQUENCE LISTING

The patent contains a lengthy "Sequence Listing" section. A copy of the "Sequence Listing" is available in electronic form from the USPTO web site (http://seqdata.uspto.gov/sequence.html?DocID=6294328B1). An electronic copy of the "Sequence Listing" will also be available from the USPTO upon request and payment of the fee set forth in 37 CFR 1.19(b)(3).

What is claimed is:

1. A method of evaluating the strain variation of a first strain of *Mycobacterium tuberculosis,* comprising the step of determining the nucleotide sequence of said first strain at positions in the complete sequence of the genome thereof, that correspond to positions where *M. tuberculosis* strains CDC 1551 and H37Rv differ as to their respective nucleotide sequences, and determining whether the nucleotide sequence of said first strain shows greater homology, at said positions, to the nucleotide sequence of strain CDC 1551 or H37Rv.

2. The method of claim 1, wherein said strain variation is evaluated for virulence.

3. The method of claim 1, wherein said nucleotide sequence of strain H37Rv is SEQ ID No.1.

4. The method of claim 1, wherein said nucleotide sequence of strain CDC 1551 is SEQ ID No.2.

5. The method of claim 1, wherein said strain variation comprises one or more single nucleotide polymorphisms.

6. The method of claim 1, wherein said strain variation comprises a nucleotide sequence of said first strain that differs at one or more positions in a DNA region encoding a protein or in a non-coding DNA region.

7. The method of claim 6, wherein said strain variation is in an encoding DNA region.

8. The method of claim 6, wherein said strain variation is in a non-coding DNA region.

9. The method of claim 7, wherein said variation is in a DNA region encoding a cell wall component.

10. The method of claim 9, where in said cell wall component contributes to pathogenicity during infection of a host with said strain.

11. The method of claim 9, wherein said cell wall component contributes to inflammation during infection of a host with said strain.

\* \* \* \* \*